United States Patent
Munn

(10) Patent No.: US 10,456,496 B2
(45) Date of Patent: Oct. 29, 2019

(54) SYSTEM AND METHOD OF DISINFECTING SURFACES WITHIN AND AROUND VANITY MIRRORS

(71) Applicant: STERILUMEN, INC., Tarrytown, NY (US)

(72) Inventor: Max Munn, Tarrytown, NY (US)

(73) Assignee: SteriLumen, Inc., Tarrytown, NY (US)

( * ) Notice: Subject to any disclaimer, the term of this patent is extended or adjusted under 35 U.S.C. 154(b) by 0 days.

(21) Appl. No.: 16/173,164

(22) Filed: Oct. 29, 2018

(65) Prior Publication Data

US 2019/0083673 A1 Mar. 21, 2019

Related U.S. Application Data

(63) Continuation of application No. 16/057,433, filed on Aug. 7, 2018, and a continuation-in-part of
(Continued)

(51) Int. Cl.
*A61L 9/20* (2006.01)
*A61L 2/26* (2006.01)
(Continued)

(52) U.S. Cl.
CPC ............ *A61L 9/20* (2013.01); *A47B 67/005* (2013.01); *A47G 1/02* (2013.01); *A61L 2/10* (2013.01);
(Continued)

(58) Field of Classification Search
CPC .................................. A61L 2/10; A45D 42/00
(Continued)

(56) References Cited

U.S. PATENT DOCUMENTS 3,776,694 A * 12/1973 Leittl ..................... A61L 2/10
312/206
6,773,682 B1 8/2004 Benda
(Continued)

FOREIGN PATENT DOCUMENTS

CN 202526007 11/2012
CN 202629828 12/2012
(Continued)

OTHER PUBLICATIONS

UV Antimicrobial Devices Used to Combat HAIs in Medical Facilities http://www.iuvanews.com/stories/122716/uv-antimicrobial-devics-used-combat-hais.shtml.

*Primary Examiner* — Michael Maskell
(74) *Attorney, Agent, or Firm* — Myron Greenspan; Lackenbach Siegel LLP

(57) ABSTRACT

A disinfecting vanity mirror includes a substantially enclosed cabinet having top, a bottom, side and rear walls and a mirror panel as the front wall when mounted to form an enclosed space or chamber. The top and bottom walls include passageways to allow vertical air flow through the enclosed space to allow air to enter through the bottom wall to rise and exit through the top wall. Sources of UV light are provided both within and below the cabinet to sanitize the air moving upwardly through the plenum space and below the vanity mirror to expose interior surfaces and exterior surfaces below the cabinet such as sinks and countertops. A controller is programmed to interrupt or discontinue the generation of UV light when a motion detector senses motion in proximity to the mirror and/or in accordance with a programmed sequence of on and off times.

18 Claims, 9 Drawing Sheets

Related U.S. Application Data application No. 15/601,607, filed on May 22, 2017, now Pat. No. 10,039,853, and a continuation-in-part of application No. 15/418,231, filed on Jan. 27, 2017, now Pat. No. 9,724,442.

(51) Int. Cl.
*A61L 2/10* (2006.01)
*A47B 67/00* (2006.01)
*A47G 1/02* (2006.01)
*A47G 1/06* (2006.01)

(52) U.S. Cl.
CPC .............. *A61L 2/26* (2013.01); *A47G 1/0622* (2013.01); *A61L 2202/11* (2013.01); *A61L 2209/12* (2013.01); *A61L 2209/15* (2013.01)

(58) Field of Classification Search
USPC ....................... 250/432 R, 435, 504 R, 492.1
See application file for complete search history.

(56) References Cited

U.S. PATENT DOCUMENTS

| | | | |
|---|---|---|---|
| 8,193,515 B2* | 6/2012 | Kreitenberg | A61L 2/10 250/455.11 |
| 8,662,705 B2 | 3/2014 | Roberts | |
| 8,900,518 B2 | 12/2014 | Seck | |
| 9,308,289 B2* | 4/2016 | Graff | A61L 9/20 |
| 9,480,768 B2 | 11/2016 | Krosney et al. | |
| 9,724,442 B1* | 8/2017 | Munn | A61L 2/10 |
| 2002/0098127 A1* | 7/2002 | Bollini | A61L 9/20 422/121 |
| 2007/0053188 A1 | 3/2007 | New et al. | |
| 2008/0008620 A1* | 1/2008 | Alexiadis | A61L 2/10 422/24 |
| 2009/0041538 A1* | 2/2009 | Berger | E06B 3/9684 403/231 |
| 2009/0291029 A1 | 11/2009 | Ogasawara | |
| 2010/0097013 A1* | 4/2010 | Inskeep | A61L 2/10 315/360 |
| 2010/0296298 A1* | 11/2010 | Martin, Jr. | A45D 42/10 362/311.06 |
| 2012/0199005 A1 | 8/2012 | Koji et al. | |
| 2012/0261593 A1* | 10/2012 | Noori | A61L 2/10 250/492.1 |
| 2013/0214174 A1* | 8/2013 | Domenig | A61L 2/10 250/455.11 |
| 2014/0060104 A1* | 3/2014 | Shur | A61L 2/10 62/264 |
| 2015/0320209 A1* | 11/2015 | Hasselback | H04N 5/2251 348/151 |
| 2015/0360606 A1 | 12/2015 | Thompson et al. | |
| 2016/0074546 A1* | 3/2016 | Rizzone | A61L 2/10 250/455.11 |
| 2017/0007736 A1 | 1/2017 | Engelhard | |
| 2017/0105554 A1* | 4/2017 | Forrest | A47G 1/1686 |
| 2017/0202988 A1* | 7/2017 | Clark | A61L 2/10 |
| 2018/0214595 A1 | 8/2018 | Munn | |

FOREIGN PATENT DOCUMENTS

| | | | |
|---|---|---|---|
| CN | 202908345 | | 1/2013 |
| CN | 203633880 | | 6/2014 |
| CN | 104524607 | * | 4/2015 |
| CN | 104524607 A | * | 4/2015 |
| CN | 205561091 | | 9/2016 |
| KR | 20120133286 | | 12/2012 |

* cited by examiner

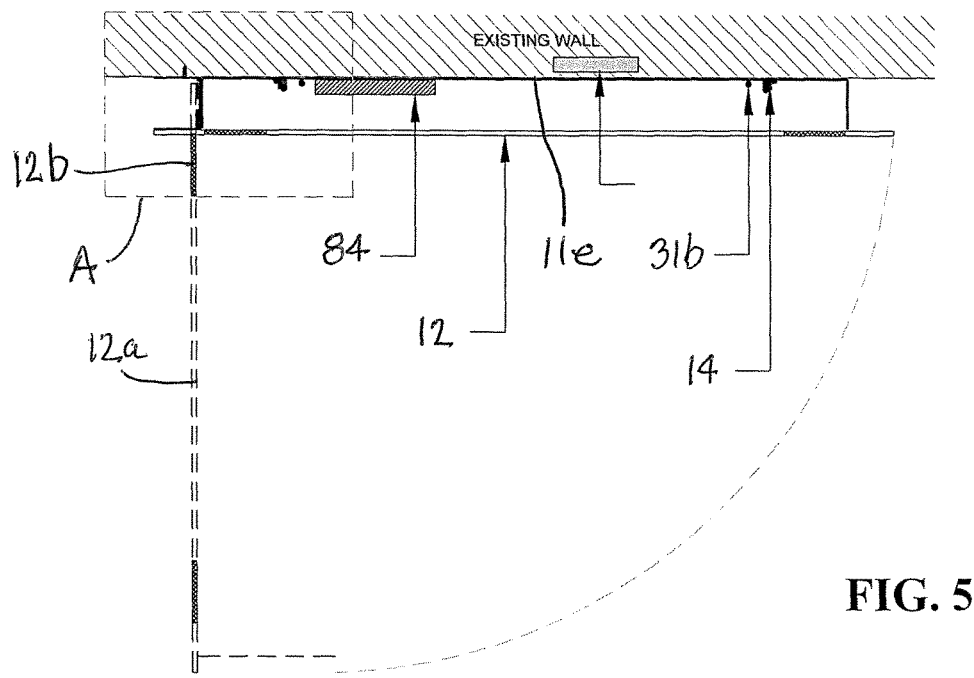
FIG. 5
FIG. 6
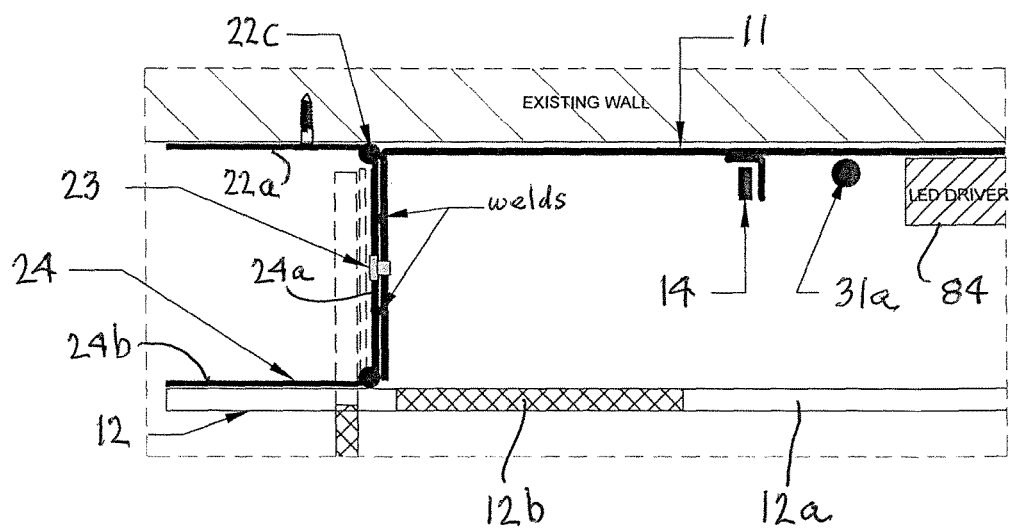

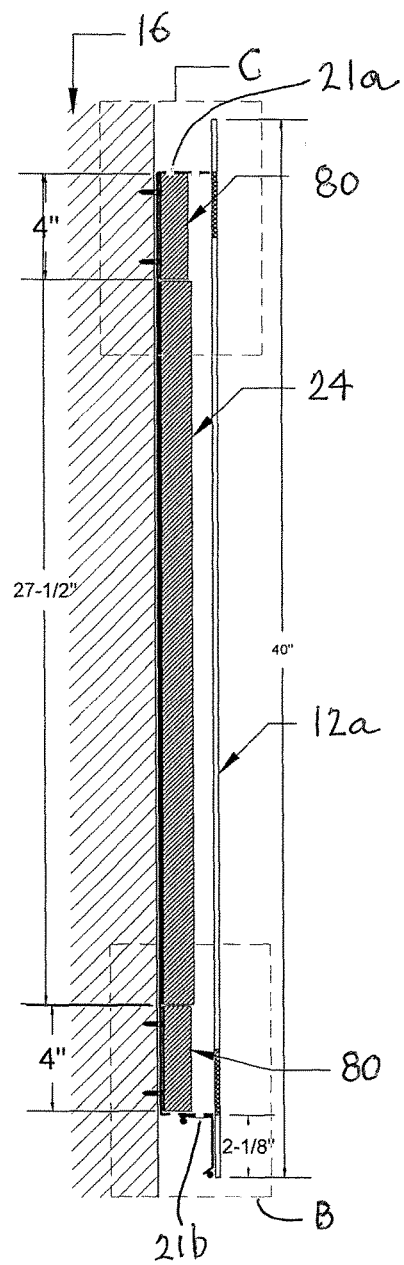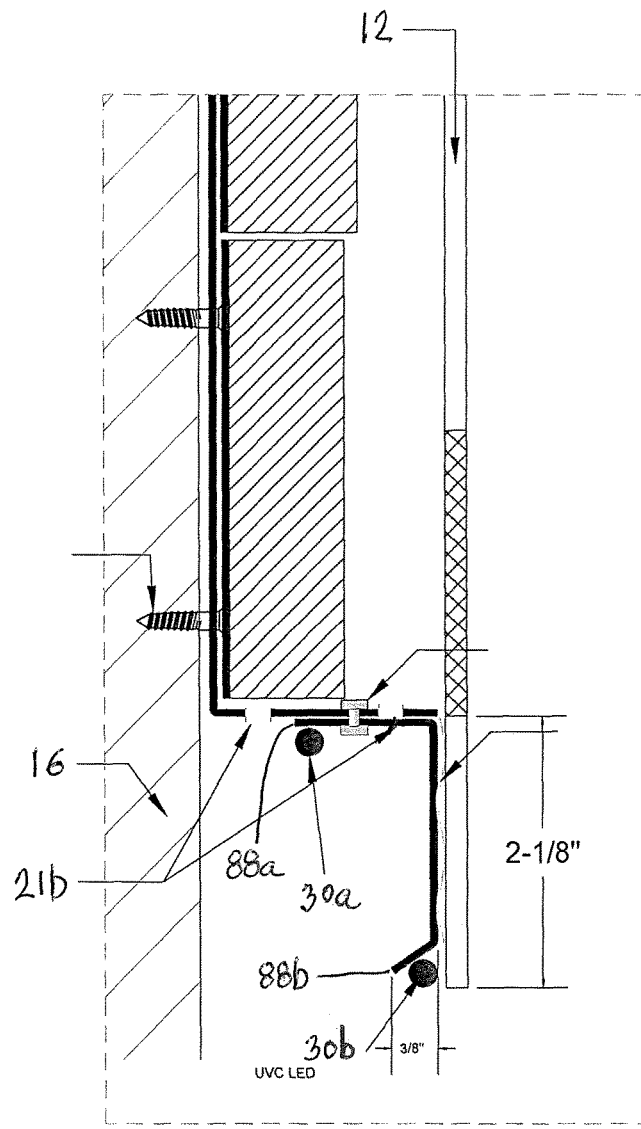
FIG. 7                    FIG. 8

SYSTEM AND METHOD OF DISINFECTING SURFACES WITHIN AND AROUND VANITY MIRRORS

BACKGROUND OF THE INVENTION

1. Field of the Invention

This invention generally relates to vanity mirrors and, more specifically, to hazard-free vanity mirrors that disinfect and purify air both inside and outside vanity mirror cabinets by exposing pathogens to a source of ultraviolet (UV) light within the spectral range of 260-280 nm for use in medical and other facilities.

2. Description of the Background Art

Health care-acquired infections (HAIs) in hospitals, assisted living facilities, etc., are serious health problems. It has been estimated that HAIs cause or contribute in excess of 99,000 deaths annually in the United States. The Center for Disease Control (CDC) reports 1 in 25 patients will contract at least one infection during their stay. Various bacteria become immune or resistant to disinfectants applied to surfaces in hospitals and other medical facilities, these bacterias commonly cause what are being referred to as "staph" infections because they are resistant to many chemical disinfectants used to clean counter tops and other surfaces in hospital rooms and the like. The general problem is discussed, for example, in the Official Publication of the International Ultra Violet Association, IUVANews. http://www.iuva.org/Publications. These infections are considered preventable. In 2011 the federal government stopped reimbursing hospitals for the care of patient that acquired an infection during their stay. Additional penalties for high infection rates have since been added that are in some situations as much as 40% of the overall revenue.

One of the hurdles to success are multi drug resistant organisms (MDRO) that are resistant to standard disinfection products and practices. This has opened the door for new technologies such as ultraviolet germicidal irradiation (UVGI) that primarily uses short-wavelength ultraviolet (UV-C) light to kill or inactivate microorganisms such as bacteria, viruses, molds and other pathogens.

Each year over 1,400,000 patients contract diseases unrelated to their initial stay at a hospital. Approximately 100,000 Americans die each year for this reason. The cost, both emotionally and financially is staggering and difficult to calculate.

The greatest concentration of pathogens within a hospital room occurs at the surface in the area surrounding the sink in the bathroom. Specifically, the faucet and the handles and the surface between these controls, and the back splash behind the sink, including the wall surface just above the sink is the most infected area in the typical hospital room.

Various UV devices have been proposed to reduce infectious pathogens. For example, bathrooms in airplanes have started to use UV LED strips to reduce pathogens while in flight. Other facilities are being outfitted with various devices to expose pathogens to UV light sources. However, UV light sources have generally been independent or stand alone devices that are specifically designed for intermittent applications.

SUMMARY OF THE INVENTION

In order to address the above and other problems associated with sanitizing or sterilizing airborne pathogens it is an object of the invention to provide a disinfecting vanity mirror that serves the additional function of exposing airborne pathogens both inside and outside vanity mirror cabinets, and pathogens on surfaces such as countertops, to ultraviolet (UV) light to destroy or neutralize such pathogens and makes them ineffective or less effective.

It is another object of the invention to provide a disinfecting vanity mirror as in the previous object that meets infection control requirements and is simple in construction and economical to manufacture.

It is still another object of the invention to provide a disinfecting vanity mirror as in the previous objects that is simple and convenient to install above sinks, countertops and other areas in medical and other facilities that require surface and air purification and disinfection.

It is yet another object of the invention to provide disinfecting vanity mirror of the type under discussion that promotes and accelerates the flow of air to be sanitized or sterilized to cause it to rise by convection or otherwise past a UVC source of light.

It is an additional object to the invention to provide a disinfecting vanity mirror that incorporates a UVC source of light that is safe to occupants, effective, non-obtrusive and aesthetically pleasing and provides continuous and reliable anti-bacterial sanitizing action both by being in proximity to a countertop and by re-cycling air to insure enhanced exposure of bacteria to UV radiation.

It is still an additional object of the invention to provide a method of sanitizing or disinfecting airborne bacteria and surfaces by incorporating a UVC light source within the mirror cabinet and along a bottom edge of a vanity mirror above a sink and/or countertop (e.g. 10" above the surface) or in other areas or surfaces that require sanitizing or disinfecting.

It is yet an additional object to pivotally mount the vanity mirror along one vertical edge so that it can be pivoted away from the mounting surface to provide access for cleaning that normally covered or hidden surface.

To achieve the above and other objects a disinfecting vanity mirror comprises a substantially enclosed cabinet having top, bottom, side and rear walls and a mirror panel as a front wall when mounted on a wall. The cabinet forms a substantially enclosed space or plenum defining a vertical direction extending between the top and bottom walls when the cabinet is mounted on a wall. At least one UV light source is provided within the enclosed space to sanitize air and surfaces within the enclosed space when air rises in proximity to the UV light source to expose the air flow to UV light. The top and bottom walls are provided with at least one air passageway in each of the top and bottom walls to allow vertical air flow through the passageways and through the enclosed space along the vertical direction. At least one micro-fan is advantageously provided above the air passageways for enhancing vertical air flow.

A method of disinfecting or sterilizing air in medical facilities, workspaces and other chambers having vanity mirrors comprises the steps of mounting a substantially enclosed vanity mirror forming an enclosed space defining a vertical direction above a sink and/or counter-top surface and providing at least one UV light source mounted within the enclosed space to sanitize air and surfaces within the enclosed space. UV light sources are also preferably provided below the mirror cabinet to sanitize surfaces such as sinks, counter-tops etc. Preferably, air is drawn through the enclosed space, such as with an exhaust fan, to promote vertical air flow through the enclosed space to enhance exposure of the air flow to the UV light source.

Motion is advantageously detected in proximity of the vanity mirror to control the UV light source to prevent excessive exposure to individuals in proximity to the vanity mirror.

BRIEF DESCRIPTION OF THE DRAWINGS

Those skilled in the art will appreciate the improvements and advantages that derive from the present invention upon reading the following detailed description, claims, and drawings, in which:

FIG. 5 is a top plan view of the mirror shown in FIGS. 3 and 4, with the mirror panel in a closed position and, in phantom outline, in the open position to provide access to the interior of the cabinet;

FIG. 6 is an enlarged view of detail A shown in FIG. 5;

FIG. 7 is a side elevational view, in vertical section, of the cabinet shown in FIGS. 3 and 4;

FIG. 8 is an enlarged view of detail B shown in FIG. 7;

DESCRIPTION OF PREFERRED EMBODIMENTS

The approximately twenty most prevalent and dangerous pathogens in hospitals that proliferate around sinks and counter-top surfaces can be very significantly reduced when exposed to ultra-violet waves especially in the spectral range of 260-280 nanometers, a fact that is now well documented. The UV diodes that generate this effective range of wave lengths (referred to as UVC waves) have in the last few years become commercially available.

A UV light generating vanity mirror that is also a lighting fixture has been developed that is:
 a. Aesthetically acceptable;
 b. Easy to install;
 c. Provides 99.99% destruction of pathogens;
  when used for approximately 45 minutes over a 24-hour period;
 d. Entirely safe;
 e. The back of the unit is easily accessible for maintenance and cleaning; and
 f. Serves both as a wall mirror and a lighting fixture.

The unit is hinge-mounted, and somewhat similar to the permanently mounted, back-lit electrified mirrors that applicant is currently selling to the hotel industry.

Figure 1:
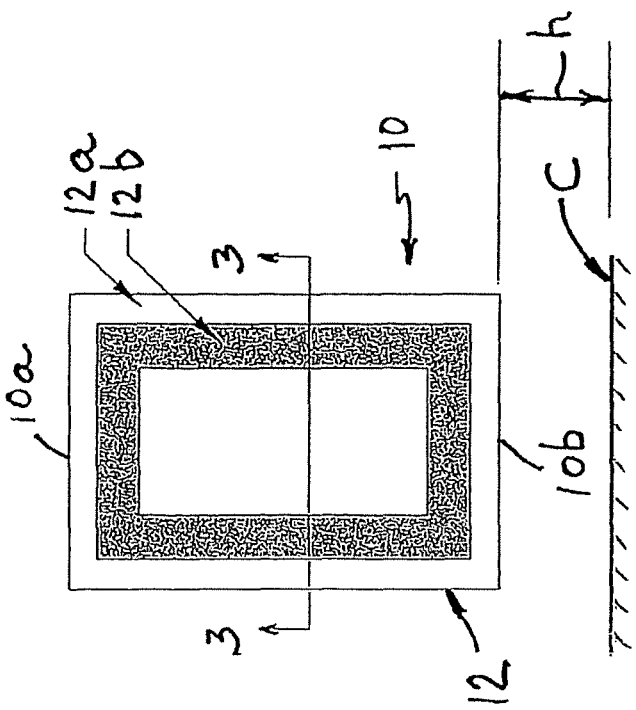
FIG. 1 is a front elevational view of a disinfecting vanity mirror in accordance with the present invention.
Figure 3:
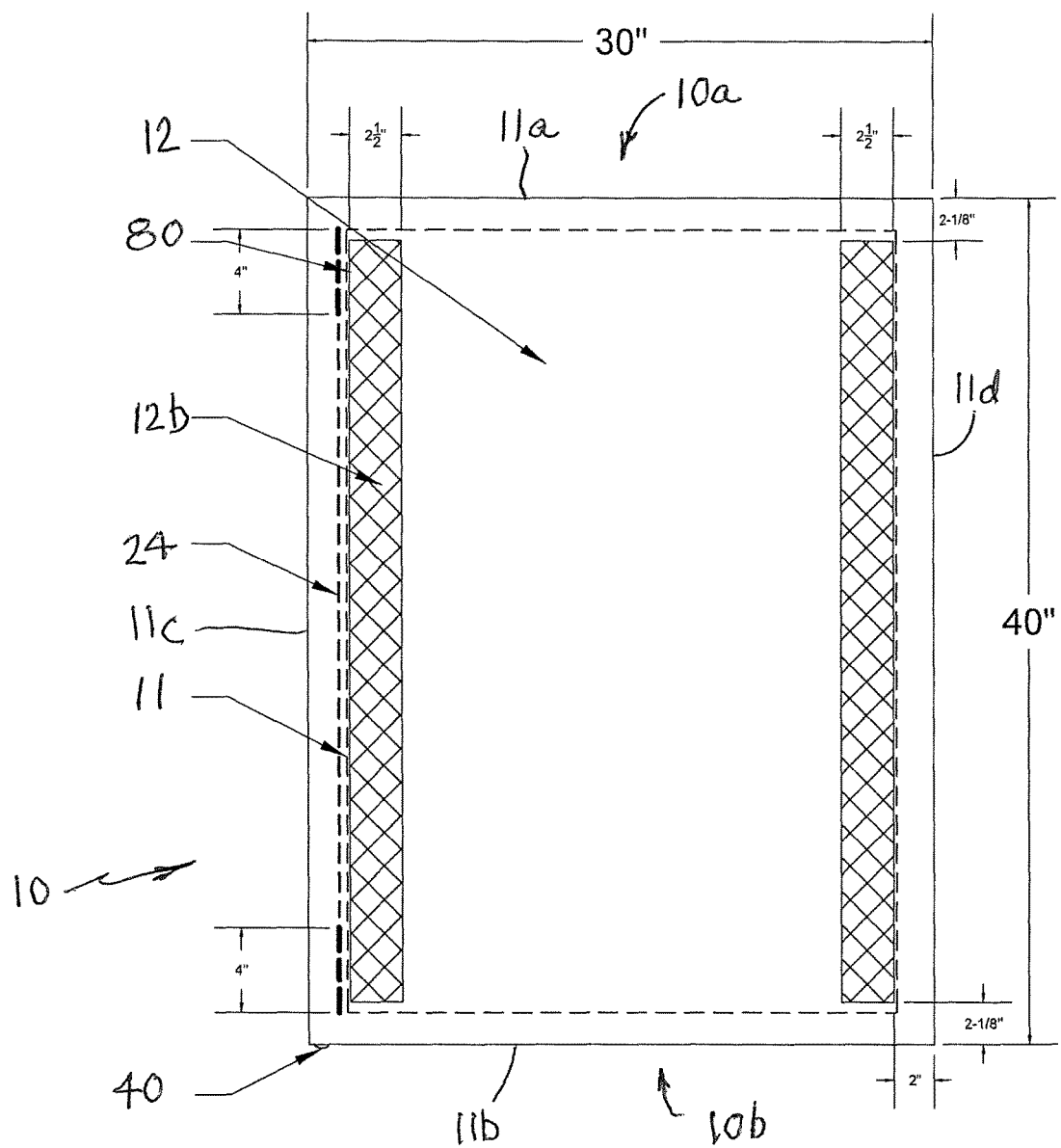
FIG. 3 is an enlarged front elevational view of the invention shown in FIGS. 1 and 2.

Referring now specifically to the figures, in which the identical or similar parts are designated by the same reference numerals throughout, and first referring to FIG. 1, one embodiment of a disinfecting vanity mirror in accordance with the invention is generally designated by the reference numeral 10.

The mirror 10 is generally rectangular in shape, as shown, and includes a top end 10a and a bottom end 10b. The vanity mirror 10 includes a substantially enclosed cabinet 11 having top, bottom, left, right and rear walls 11a, 11b, 11c, 11d and 11e, respectively. The cabinet 11 also has a front wall in the form of a mirror panel 12 having a central reflective surface 12a and a frosted peripheral strip 12b. The mirror panel 12 may be 3/16" clear hospitality grade mirror. The mirror 10 may be similar in appearance to back-lit mirrors of the type manufactured by MunnWorks LLC in Mount Vernon, N.Y. The LED Strip 14 emits visible light, for example, at 2700 k, that provides lighting through the frosted peripheral strip 12b in a conventional manner.

Figure 2:
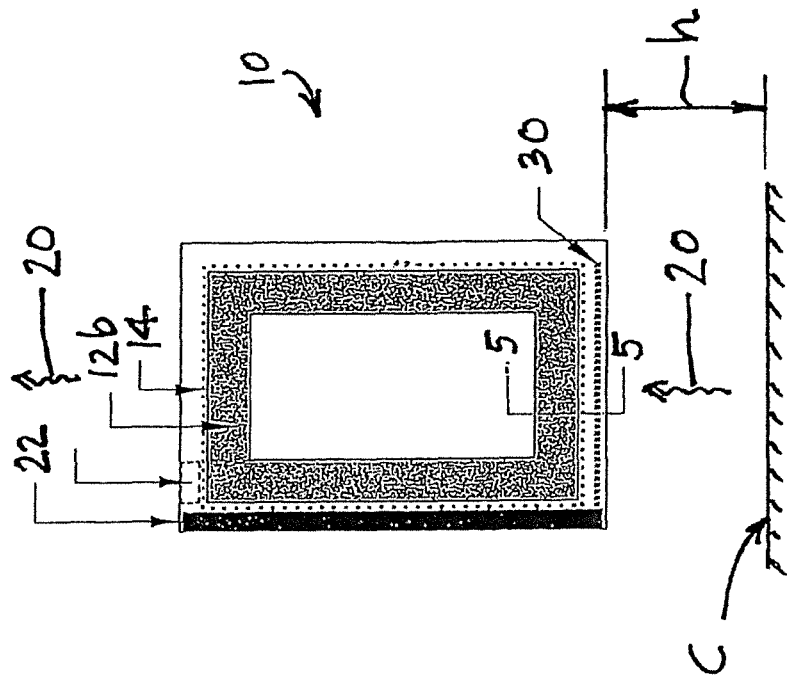
FIG. 2 is similar to FIG. 1 but shows additional details.

Referring to FIGS. 1, 2 and 5, the mirror 10 is typically mounted on a wall or vertical surface 16 above a sink or countertop C. When mounted on the surface 16 the cabinet walls 11a-11e and the mirror panel 12 together form a substantially enclosed space or plenum 13 forming an air shaft defining a vertical direction V (FIG. 1) extending between the top and bottom ends 10a, 10b. The plenum 13, according to the invention, provides a substantially vertical air shaft, passageway or column for air to rise by entering through the bottom end 10b and exiting through the top end 10a as suggested by the arrow 20 in FIG. 2. Additional details will be provided below in connection with FIGS. 4, and 7-9. While the height "h" of the mirror 10 above the countertop C is not critical a height of 10" is typical and will provide beneficial germicidal results by the application of the present invention.

Referring specifically to FIGS. 3-11, a method of mounting the mirror 10 is illustrated. A chassis hinge 22 is provided that includes a first hinge plate 22a and a second hinge plate 22b, the two hinge plates being joined for relative pivotal rotation at 22c. As shown in FIGS. 5 and 6, the hinge plate 22a is connectable to the wall or surface 16 to be generally coextensive with the wall 16 while the hinge plate 22b is provided at one lateral wall, shown in FIGS. 3 an 4 to be the left side wall 11c, for attachment thereto by any suitable fasteners, such as bolts or rivets 23. The hinge 23 may be a single long hinge, such as a piano hinge, or a plurality of spaced shorter hinges along the associated lateral or side wall of the cabinet.

Figure 10:
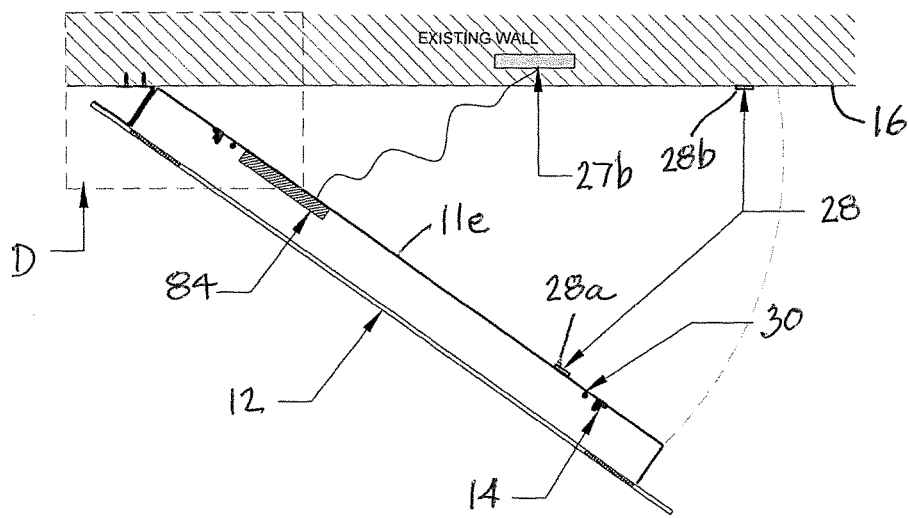
FIG. 10 is similar to FIG. 5, showing the cabinet in a pivoted extended position to provide access to the surface normally covered by or behind the cabinet.

Referring to FIG. 10, suitable means 28 is advantageously provided to prevent inadvertent movement and separation of the cabinet 11 from its retracted position shown in FIGS. 5 and 6. Such means may include a magnet 28a mounted on the back surface of the rear wall 11e for cooperation with a suitably positioned element 28b mounted on the wall 16 to register with the magnet 28a. The elements 28a, 28b can be interchanged as to where they are mounted. The cooperating element 28b may be a suitably polarized magnet or ferromagnetic disc or plate that is magnetically attracted to the magnet 28a.

Any suitable or conventional hinge can be used to mount the mirror panel 12 to the cabinet 11. However, as shown in FIG. 6, a U-shaped plastic hinge 24 is preferred for this application to eliminate or minimize the number of interstices or crevasses in which pathogens can become lodged and multiply. A first portion 24a of the plastic hinge is secured to the hinge plate 22b while a second portion 24b is secured to the mirror panel 12.

A feature of the mirror 10 is the integration of a source of UV light 30 that extends along at least a portion but preferably along the entire width of the bottom end 10b to expose pathogens to UV radiation and the heat generated by the LEDs also promote convection of air and updraft efficiency by locally heating air proximate to the bottom end 10b to generate the airflow 20 (FIG. 2). The UV light sanitizes air moving upwardly through the enclosed space or plenum space 13, created to simulate a chimney effect, and this promotes movement of air past the UV light source 30. Also, by providing the UV light source 30 in proximity to the lower end or edge of the mirror 10 the UV light will be efficient in sanitizing or neutralizing pathogens below the cabinet such as a sink and/or countertop C.

The UV light source 30 is in the form of a strip of LEDs that emit UV light within the range of 200-280 nm and, preferably within the range of 240-280 nm. As indicated in the IUVANews publication ultraviolet radiation is defined most broadly as consisting of radiation within the range of 10-400 nm. However, most effective for germicidal applications is the short wave ultraviolet light normally designated as UV-C. UV-C includes wavelengths of 100-280 nm, although 240-280 nm are most effective for sanitizing or sterilizing airborne pathogens. UV light in that range is most efficiently absorbed by DNA, with maximum absorption being at approximately 260 nm. UV-C has been used for air purification, sterilization and disinfection. High intensity UV at 240-280 nm radiation can destroy DNA in living micro organisms. The effectiveness of the UV radiation is directly related to the intensity and exposure time(s). The present disinfecting vanity mirror 10 is convenient, inexpensive and an effective way to neutralize micro-organisms and pathogens by constantly circulating and recycling the air that passes through the plenum space 13, forcing the air to be continuously exposed to the UV LED-strip 30.

To enhance the quantity of air moved through the plenum space 13 the vanity mirror 10 may also advantageously utilizes a thermal strip (not shown) for providing additional heating of the air in proximity to the UV LED strip 30 at the bottom end 10b of the mirror. Between the heating of the air by the UV LED strip 30 and a thermal strip the air below the vanity mirror 10 can be heated more quickly and more vigorously and to a higher temperature. This causes higher quantities of air to move up through the plenum space 13 thereby exposing increased numbers of pathogens to the UV light source 30.

By using a mirror 10, for example, that is 24-30" wide and 34-40" tall at a height of approximately 10" above a sink or countertop C most harmful pathogens can be neutralized if power is applied for only approximately 30 minutes per day. The LED strips are conventionally powered when a wall switch is turned on (e.g. in a bathroom where a sink, countertop and vanity mirror are typically situated). Normally the vanity is used for at least 30 minutes per day.

The disinfecting vanity mirror 10 is, therefore, an inexpensive and reliable way of exposing air contaminated with pathogens to UV-C light on an ongoing or continuing basis when energized to increase the effectiveness of the sanitization and decontamination of airborne and surface of microorganisms found on countertops.

By locating the UV light source 30 along the bottom edge of the mirror, behind the mirror panel 12, a number of advantages are achieved. The user is protected from UV radiation that can be harmful to the user's eyes and skin.

Also, the light does not reflect onto the mirror to avoid undesirable shades or tones or lighting distortions. Using LED light strips considerably increases the life of the sources over conventional UV sources, such as mercury lamps or bulbs. By integrating the UV light source into the vanity mirror there is no need to have an operator use specialized UV equipment to periodically sanitize a facility.

An additional UV-LED strip (not shown) may be provided along the vertical edge of the mirror proximate to the mirror panel hinge 24 where buildup of bacteria is also likely to proliferate and manual maintenance may be most problematic. The additional UV-LED strip serves to sanitize bacteria that may have attached to the surface of the hinge to ensure that the hinge remains bacteria free with or without manual maintenance. Suitable heat sinks may be provided to prevent excessive heat from developing in the UV-LED strips to promote reliability and longevity of the UV-LED strips by preventing excessive heat buildup.

Figure 4:
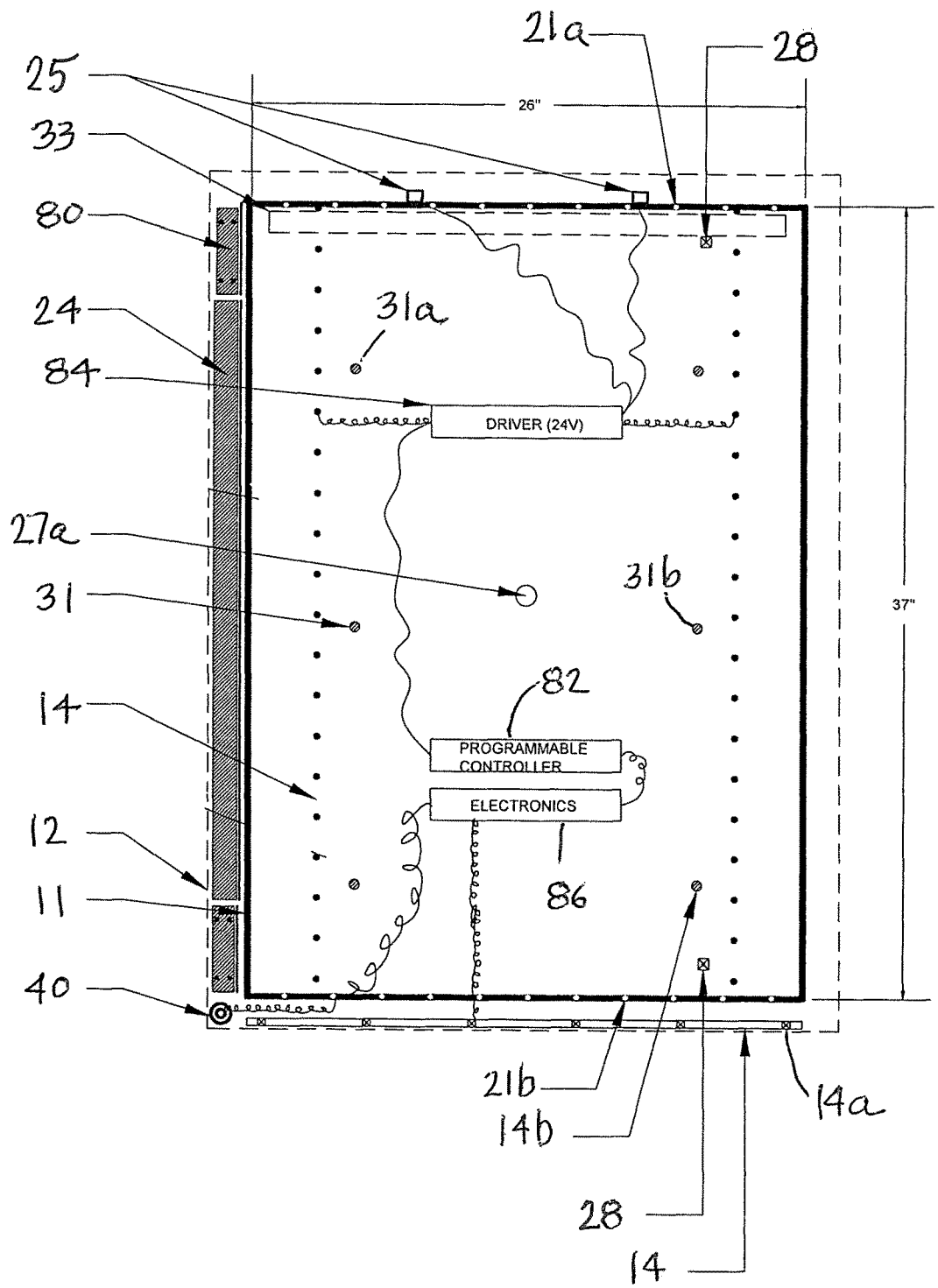
FIG. 4 is similar to FIG. 3 with the mirror panel removed to expose interior electronics including LED light strips, UV light strips, both inside and outside the mirror cabinet, exhaust fans and control circuitry.

Another important feature of the invention is the provision of at least one UV light source 31 within the enclosed space 13. A plurality of such UV light sources may be provided within the enclosed space. FIG. 4 shows one exemplary arrangement of interior UV light sources, may be arranged in columns represented by light sources 31a, 31b. However, the specific arrangement of the internal UV light sources is not critical and a plurality of substantially vertical columns of spaced UV light LEDs or other light sources may be provided. Other arrangements of light sources may be used to expose the interior surfaces, including shelf surfaces within the cabinet 11. As shown in FIG. 4, the two columns of spaced UV light sources are positioned to be generally in proximity to the corners at the lateral sides of the cabinet that may be more difficult to clean and more susceptible for buildup of pathogens.

The UV-LED strips may be replaced by UV mercury lamps or bulbs in the form of miniature florescent tubes that can be mercury lamps, xenon lamps or any lamp with UV wave generating components, waves or light. The invention contemplates the use of any UV source that generates suitable UV light to disinfect surfaces within or inside the cabinet, surfaces on to the mirror mounting hinge and surfaces below the cabinet 11 such as sinks and countertops.

In order to promote or enhance the flow of air 20 (FIG. 2) through the enclosed space or plenum 13, and expose the air flow to the internal UV light sources 31, the top and bottom walls 11a, 11b are advantageously provided with air passageways 21 to allow vertical air flow through the enclosed space or plenum 13 along the vertical direction when the cabinet is mounted on a wall as shown. The passageways may be in the form of a plurality of openings or perforations 21a, 21b. Advantageously, in order to promote or enhance air flow through the enclosed space 13 one or more fans can be used to create a lower than atmospheric pressure above the top wall 11a or higher than atmospheric pressure below the bottom wall 11b. In FIG. 4, two micro exhaust fans 25 are provided above the top wall 11a in registry with at least some of the perforations 21a. Any other means can be used to achieve the same or similar result.

Figure 9:
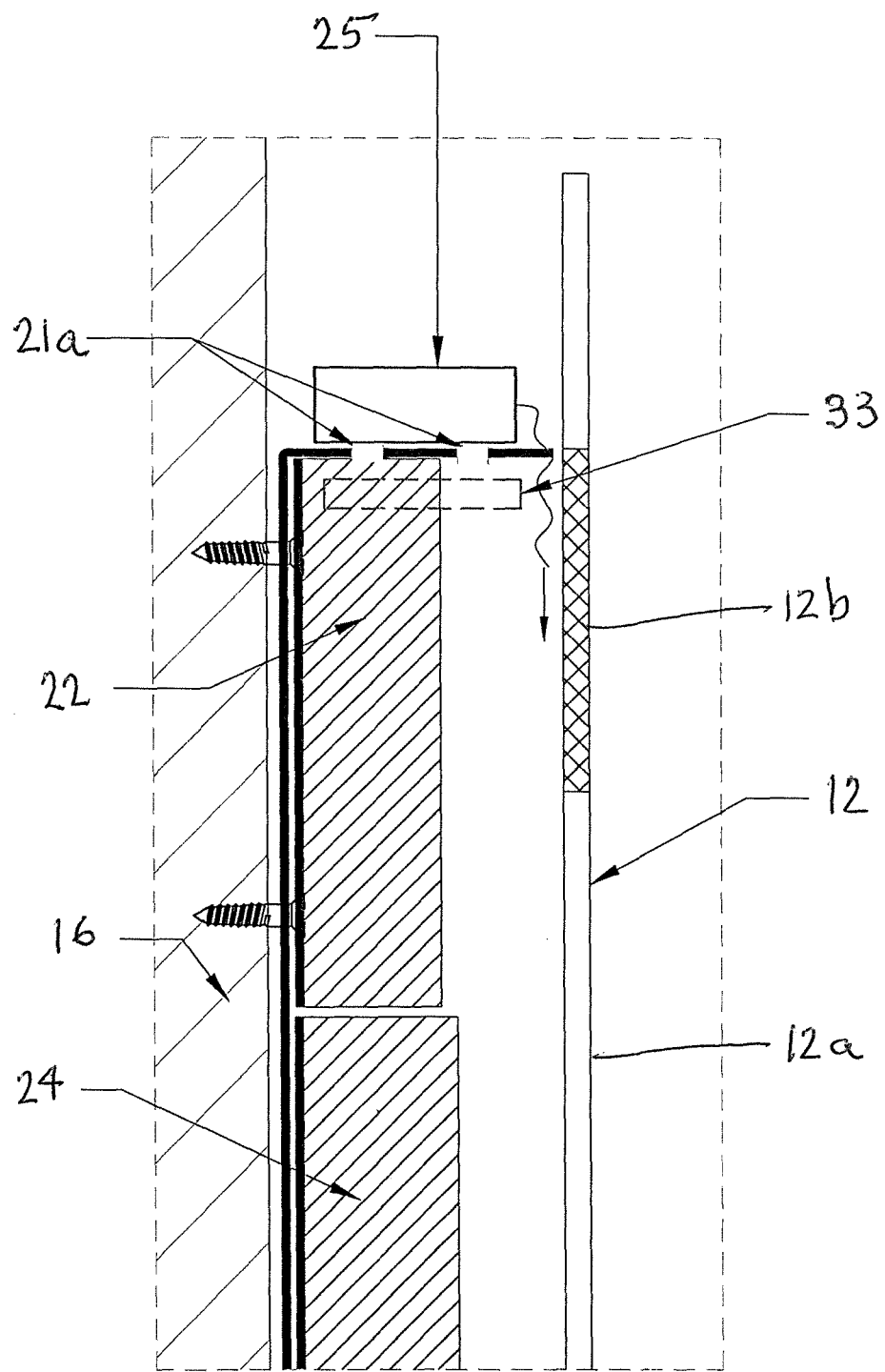
FIG. 9 is an enlarged view of detail C shown in FIG. 7.

In order to improve air quality and further remove bacteria and other pathogens replaceable HEPA filters 33 may be provided along the passageways or perforations 21a and/or 21b in the path of air flow. In FIGS. 4 and 9 a HEPA filter 33 is shown within the cabinet 11 upstream of the air flow.

In view of the foregoing, the present invention broadly contemplates an electric backlit mirror that is attached to a wall with a hinge for ease of movement and with UV light sources to expose and disinfect the interior surfaces in the cabinet as well as surfaces C below the cabinet 11. The driver, electronics, LED diodes, UV diodes, UV light bulbs, tubes or lamps may all be mounted within the plenum space 13

Electrical connection can be made through perforation or opening 27a (FIG. 4) that is located to register with J-box 27b (FIG. 10) in the wall 16.

Figure 12:
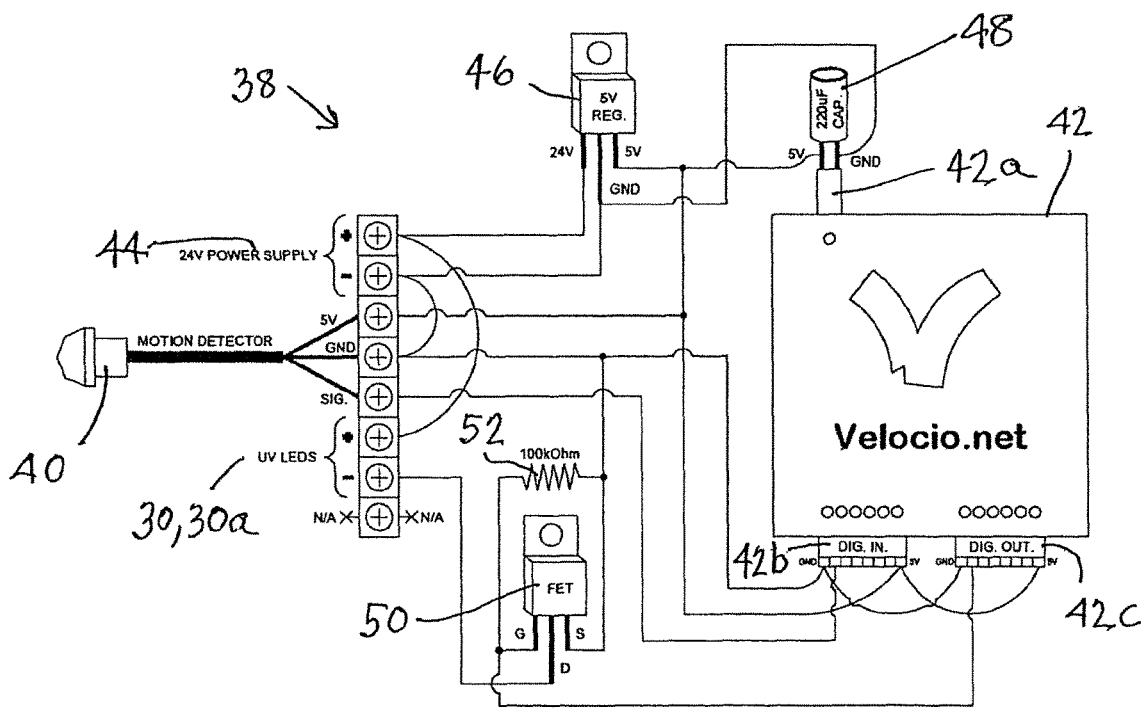
FIG. 12 is a schematic diagram of a motion control wiring circuit that can be used in connection with the aforementioned disinfecting vanity mirror embodiments for controlling or limiting excess emission of UV light to protect individuals in proximity to the mirrors.

To avoid potential safety issues to patients and occupants of the enclosures in which the mirrors are mounted from excessive exposure to UV light, the mirrors of the invention may be provided with circuitry for intermittently de-activating or interrupting the UV light sources or generators so that these are not always on to emit UV light continuously but intermittently but sufficiently to be effective for sanitizing or disinfecting the areas within the enclosure. Referring to FIG. 12, a circuit 38 is shown that can be used for this purpose. The circuit 38 is preferably also mounted behind the mirror, possibly encapsulated, to minimize the openings, traps or surface areas on which bacteria can settle and grow. Circuit 38 serves two purposes. The first is to cycle the UV light sources (e.g. 30 and 30a) in accordance with a desired or predetermined schedule, and the second is to detect motion within the enclosure where the mirror is mounted so that the UV light sources can be de-activated, interrupted or de-energized when motion in proximity to the mirror is detected. Any programmed controller can be used to provide these functions. Circuit 38, by way of example, illustrates the use of a motion detector 40 connected to a programmed controller 42. A power supply 44, such as a 24 volt source, is used to energize the circuit 38, a 5 volt regulator being used, if necessary, to generate a regulated voltage to power the programmed controller 42. A capacitor 48 connected to the controller 42 at port 42a, a field effect transistor (FET) 50 and resistor 52 are connected to input port 42b and output port 42c of the programmed controller as shown. The UV LED light sources 30, 30a are connected as shown, the components connected to the programmed controller 42 enabling the controller 42 to operate as a timer to establish predetermined time intervals, as to be described in connection with FIG. 15. FIG. 14 however, is only one configuration of a programmed controller for timing the operation of the UV-LED's although any other known timers or timing circuits may be utilized for this purpose.

Figure 13:
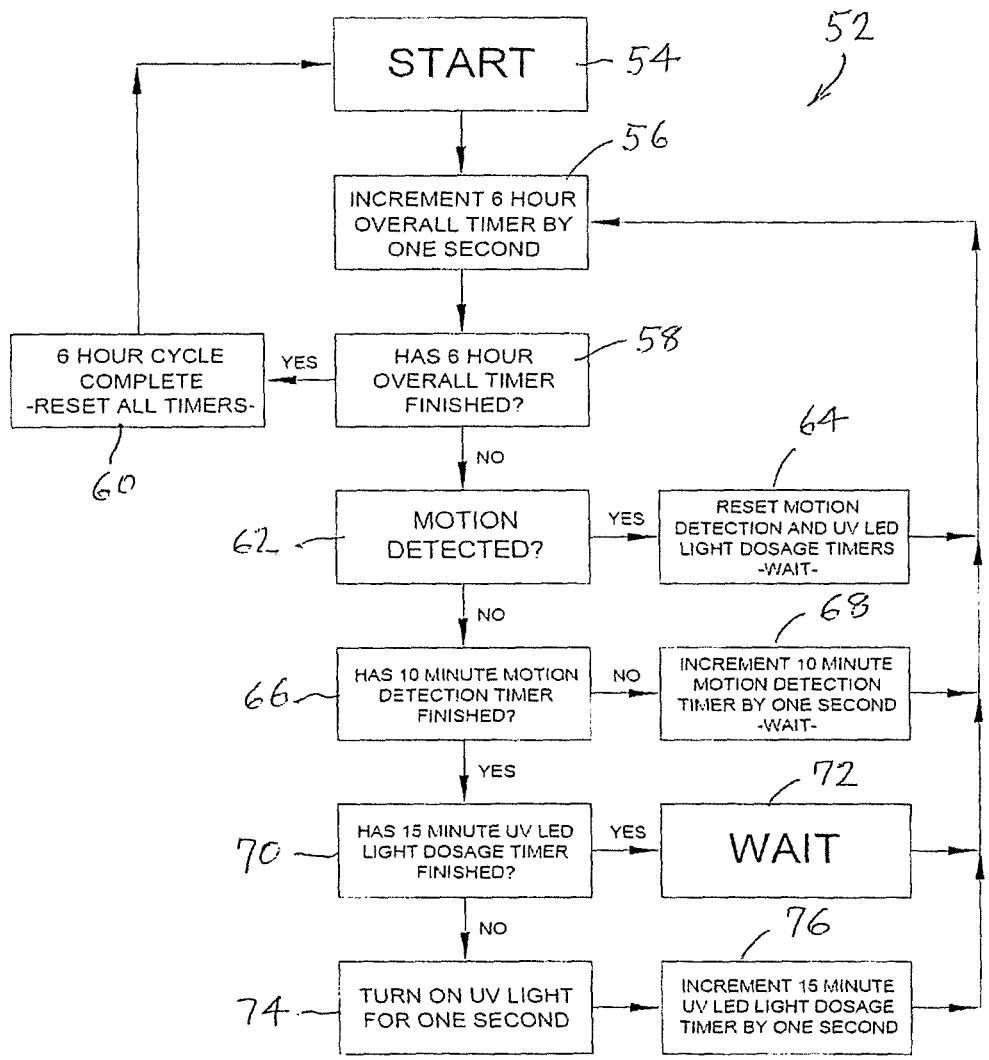
FIG. 13 illustrates a flow chart representing the operation of the programmed controller in FIG. 12 for controlling and preventing excess emission of UV light with the circuit shown in FIG. 12.

Referring to FIG. 13, a flow chart 52 is shown that illustrates the programmed protocol or logic for monitoring and controlling the UV light sources, whether they be LED's, lamps, bulbs, fluorescents, etc. Initially, the controller 42 commences operation at 54 to increment the timer in 6 hour intervals at 56. Thus, without external influences, the controller energizes the UV light sources every few hours. The UV light sources are energized several times during each 24 hour period. At 58, the controller 42 queries whether the timer has completed its programmed interval. After a 6 hour cycle has been completed all the timers are reset at 60 and the controller reverts to the start position at 54. If the 6 hour overall timer has not been completed the controller queries whether the motion detector 40 has detected any motion, at 62. If motion has been detected the motion detection and UV-LED light dosage timers are reset, at 64, and the controller reverts to incrementing the timer, at 56, to repeat the protocol. If motion has not been detected at 62 the controller queries whether a 10 minute motion detection timer has finished, at 66. If the motion detection timer has not finished the 10 minute motion detection timer is incremented by one second at 68 and the controller reverts to the programmed increment overall timer at 56. If the 10 minute motion detection timer has finished, at 66, the controller 42 queries whether the 15 minute UV-LED light dosage timer has finished, at 70. If it has finished the controller is instructed to wait, at 72, after which the hour is incremented by one second, at 56. If the 15 minute UV-LED light dosage timer has not finished, at 70, the UV light sources are turned on for one second, at 74. After the UV light has been activated, at 74, the 15 minute UV-LED timer is incremented by one second, at 76, and the 6 hour overall timer is thereafter incremented again at 56. The cycle is repeated on an ongoing or continuous basis with the program controller 42 regulating the operation or energization of the UV light sources at the preselected or desired time intervals, as may be modified by the presence of individuals sensed by the motion detector 40.

Figure 11:
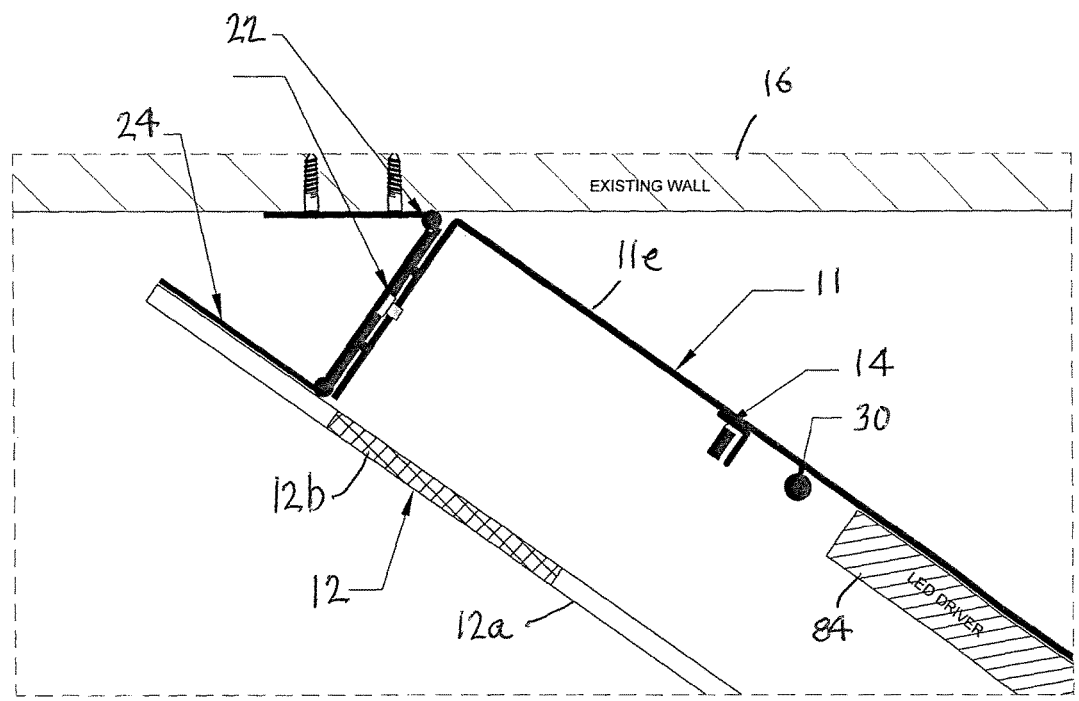
FIG. 11 is an enlarged view of detail D shown in FIG. 10.

Accordingly, the mirror panel 12 is mounted on the cabinet 11 and at least one UV light source is mounted on the bottom end of the cabinet, the UV light source being configured to direct UV light vertically downwardly to sanitize air and surfaces below the mirror panel. The vanity mirror 10 is provided with a chassis hinge 22 that enables the pivoting of the cabinet to a position or juxtaposed against the mounting surface or wall in close proximity thereto as shown, for example, in FIGS. 5-9. However, the hinge 22 allows the cabinet 11 to be pivoted away from the wall mounting surface as shown in FIGS. 10 and 11 to provide access to the surface normally covered by the cabinet when in the closed position. This allows the surface behind the cabinet to be cleaned and disinfected periodically or as often as necessary.

Referring to FIG. 4, with the mirror panel removed, a programmable controller 82 is connected to the LED light strips 14, controlled by the programmable controller 82. Electronics 86 shown in FIGS. 14 and 15 receive input from motion detector 40 and suitably actuates the UV LEDs or light source 30.

A feature of the invention is the provision of an easily replaceable or exchangeable metal flange or bracket 88 (FIG. 4) running along the bottom end or edge 11b of the cabinet 11 on which there are mounted UV LEDs, as shown in FIGS. 4, 7 and 8. The number of the UV LEDs and the power of these LEDs are selected to provide the desired UV intensity on a countertop or surface C, keeping in mind that the UV intensity is inversely propositional to the square of the distance, rapidly increasing at distances less than 1 meter. Directing the UV light downwardly or substantially downwardly increases the UV dose for effectiveness. Also, since dust and films that become deposited on the UV light sources lowers UV output these UV LEDs should normally be cleaned periodically. Also, a suitable fan or the like can be provided to blow air on the LEDs to keep them free of dust.

Referring to FIG. 4 a wall lock 28 is provided for selectively maintaining the cabinet chassis in its closed or retracted position against the wall or mounting surface to prevent the cabinet to be inadvertently pivoted outwardly as shown in FIGS. 10 and 11.

Another feature of the invention is the provision of removable metal flange 88 shown in FIGS. 4, 7 and 8. The flange or bracket is generally L-shaped in cross section and extends substantially across the entire width of the bottom end 11b of the cabinet. The flange or bracket 88 has free edges 88a and 88b as shown in FIG. 8 and one UV light source including spaced UV LEDs are mounted generally along each of the free edges 88a, 88b of the flange or bracket 88. This ensures that the UV LEDs direct UV light substantially vertically downwardly and slightly outwardly away from the wall 16 to sanitize air and surfaces C below the vanity mirror.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The invention claimed is:

1. Disinfecting vanity mirror comprising a substantially enclosed cabinet having top, bottom and lateral ends and rear and front walls when mounted on a vertical surface, said cabinet ends and said walls together forming an interior space defining a vertical direction extending between said top and bottom ends, said front wall comprising a mirror panel movable between an open position to provide access to said interior space and a closed position to substantially enclose said enclosed space; mounting means for mounting said cabinet on a wall; and at least one UV light source within said enclosed space arranged to sanitize air and surfaces within substantially said entire enclosed space when said mirror panel is in said closed position, said mounting means including a hinge at one of said one lateral ends to movably mount said cabinet between a normally closed position substantially juxtaposed against the wall and an open position to provide access to a surface normally covered by said cabinet when in said closed position, said hinge enabling independent movement of said cabinet and said mirror panel relative to said cabinet whereby said normally covered surface can be cleaned and disinfected when said cabinet is moved to said open position.

2. A disinfecting vanity mirror as defined in claim 1, further comprising means for creating a vertical flow of air within said enclosed space through at least a portion of a distance between said top and bottom ends and passing in proximity of said at least one UV light source to expose said air flow to UV light.

3. A disinfecting vanity mirror as defined in claim 2, wherein said top and bottom ends comprise top and bottom walls provided with at least one air passageway in each of said top and bottom walls to allow vertical air flow through said passageways and through said enclosed space along said vertical direction.

4. A disinfecting vanity mirror as defined in claim 3, wherein said air passageways comprise a plurality of openings or perforations.

5. A disinfecting vanity mirror as defined in claim 3, further comprising air flow enhancement means for promoting vertical air flow through said enclosed space.

6. A disinfecting vanity mirror as defined in claim 5, wherein said air flow enhancement means comprises at least one fan for enhancing said vertical air flow.

7. A disinfecting vanity mirror as defined in claim 6, wherein a plurality of fans are provided in proximity to said top wall for drawing air from said enclosed space and expelling the air to a region above said enclosed cabinet.

8. A disinfecting vanity mirror as defined in claim 1, wherein a plurality of UV light sources are provided within said enclosed space.

9. A disinfecting vanity mirror as defined in claim 8, wherein said plurality of UV light sources comprise UV LEDs spaced from each other along said vertical direction.

10. A disinfecting vanity mirror as defined in claim 9, wherein at least two spaced substantially vertical columns of spaced UV LEDs are provided.

11. A disinfecting vanity mirror as defined in claim 1, further comprising a magnetic or other wall lock for normally retaining said cabinet in said closed position and selectively enabling movement of said cabinet to an open position to expose said normally covered wall surface.

12. A disinfecting vanity mirror as defined in claim 1, wherein said source of UV light generates ultraviolet radiation within the range of 260-280 nm.

13. A method of disinfecting or sterilizing air in medical facilities, workspaces and other chambers having vanity mirrors having a cabinet and mirror panel movable relative to said cabinet to provide access to a space defined by an interior of said cabinet and to enclose said interior space of said cabinet comprising the steps of providing at least one UV light source mounted within said enclosed space arranged to sanitize air and surfaces within substantially said entire space when it is enclosed by said mirror panel; and moving said cabinet independently of said mirror panel to expose an area normally covered by said cabinet to enable cleaning and disinfecting the area normally covered by said cabinet.

14. A method as defined in claim 13 further comprising the step of drawing air through said enclosed space to promote vertical air flow through said enclosed space and enhance exposure of the air flow to said UV light source.

15. A method as defined in claim 14, further comprising the step of detecting motion in proximity of the vanity mirror to control said UV light source.

16. Disinfecting vanity mirror comprising a substantially enclosed cabinet having top, bottom and lateral ends and rear and front walls when mounted on a wall, said cabinet ends and walls together forming an enclosed space defining a vertical direction extending between said top and bottom ends, said front wall comprising a mirror panel movable between an open position to provide access to said enclosed space and a closed position to substantially enclose said enclosed space; mounting means for mounting said cabinet on a wall and including a hinge enabling independent movement of said cabinet and said mirror panel relative to said cabinet; and at least one UV light source within said enclosed space arranged to sanitize air and surfaces within substantially said entire enclosed space, wherein said top and bottom ends comprise top and bottom walls provided with at least one air passageway in each of said top and bottom walls to allow vertical air flow through said passageways and through said enclosed along said vertical direction.

17. Disinfecting vanity mirror comprising a substantially enclosed cabinet having top, bottom and lateral ends and rear and front walls when mounted on a vertical surface, said cabinet ends and said walls together forming a substantially enclosed space defining a vertical direction extending between said top and bottom ends, said front wall comprising a mirror panel; mounting means for mounting said cabinet on a wall; and at least one UV light source within said enclosed space arranged to sanitize air and surfaces within said enclosed space, and an easily-removable or interchangeable flange or bracket extending generally along said bottom end, said at least one UV light source being mounted on said flange or bracket that is configured to direct UV light substantially downwardly away from said cabinet.

18. A vanity mirror as defined in claim 17, wherein said flange or bracket is removably attached to said bottom end of said cabinet.

* * * * *